(12) United States Patent
Helquist

(10) Patent No.: US 6,730,788 B1
(45) Date of Patent: May 4, 2004

(54) PROCESS FOR 1,10-PHENANTHROLINE LIGANDS

(75) Inventor: Paul Helquist, Granger, IN (US)

(73) Assignee: University of Notre Dame, Notre Dame, IN (US)

( * ) Notice: Subject to any disclaimer, the term of this patent is extended or adjusted under 35 U.S.C. 154(b) by 0 days.

(21) Appl. No.: 09/663,626

(22) Filed: Sep. 18, 2000

Related U.S. Application Data

(60) Provisional application No. 60/159,574, filed on Oct. 18, 1999.

(51) Int. Cl.$^7$ .............................................. C07D 471/04
(52) U.S. Cl. ......................................................... 546/88
(58) Field of Search ........................................... 546/88

(56) References Cited

PUBLICATIONS

Corey et. al., "transformations in the 1, 10–Phenantrholine Series", J. Org. Chem., 30, pp. 288–290, 1965.*
Pena–Cabrera, E. et al.,.,J.Am. Chem.Soc.1996,118, 4299–4313.
E.J. Corey et al., J. Org. Chem. 1965, 30, 288–290.
S. Gladiali et al., J. Organometalic Chem., 327 (1987) C–15 C–17.
S. Gladiali et al., J. Organometallic Chem., 370(1989) 285–294.
Goodman et. Al. , J.Am. Chem.Soc.1995.117,8447–8455.
Gothelf, et al.,J.Org.Chem.1996,61, 346–355.
Weijnen et. al., "Synthesis of Chiral, 1,10–Phenanthroline Ligands and the Activity of Metal–Ion Complexes in the Enantioselective Hydrolyis of N–Protected Amino Acid Esters", J. Org. Chem. 1992, 57, 7258–7265.
Yonehara, et al., J. Org. Chem. 1999, 64, 5593–5598.
Li, et al., J. Org. Chem. 2000, 65, 3489–3496.
Chandler, C.J. et al.J.Heterocyclic Chem. 18,599 ('81).
Weijnen,J.G.J., et al. J. Org. Chem. 1992, 57,7258 ('92).
Akane, T., J. Org. Chem.1994.59,1902 ('94).
Lin, Shu–Chen, et al,J. Org. Chem.1998,63,2909 ('98).
N.A. Lange, Ed. , Handbook of Chemistry, 8th Ed., 1952.

* cited by examiner

*Primary Examiner*—Alan L. Rotman
*Assistant Examiner*—Binta Robinson
(74) *Attorney, Agent, or Firm*—Jagtiani + Guttag

(57) ABSTRACT

Process for preparing 1,10-phenanthroline ligands represented by the formula

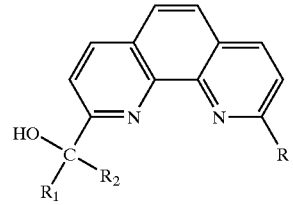

which comprises coupling a 1,10-phenanthroline of the formula

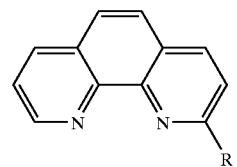

with a ketone e.g. a dialkyl, cycloalkyl or bicycloalkyl ketone with a metal coupling reagent, preferably a lanthanide II e.g. samarium II, wherein R is hydrogen, alkyl, cycloalkyl, bicycloalkyl or aryl e.g. phenyl. The hydroxy group of the product may be converted to derivatives e.g. esters and ethers to form additional ligands. The hydroxy group of the product also may be converted to a reducible group e.g. the methoxy ether and the ether replaced by hydrogen in the reduction. The reduction product wherein R of the starting material is hydrogen can be coupled with a ketone in the process to provide 2,9-disubstituted 1,10-phenanthroline ligands. The ligands provided are preferably in chiral form and complex with metals, e.g. transition metals, which serve as catalysts in many processes such as addition and substitution reactions.

30 Claims, No Drawings

PROCESS FOR 1,10-PHENANTHROLINE LIGANDS

CROSS REFERENCE TO RELATED APPLICATION

This application is a non-provisional application claiming the benefit of provisional application Serial No. 60/159,574 Expired filed Oct. 18, 1999.

FIELD OF THE INVENTION

This invention relates to ligands for metal catalysts. In particular, it relates to 1,10-phenanthroline ligands and to a process for preparing such ligands in chiral or achiral form.

1,10-Phenanthroline binds with almost all metals to form metal complexes and has been the subject of extensive efforts to prepare substituted derivatives for use as metal catalyst ligands especially in chiral form for use in asymmetric metal catalyzed processes. However, the development of such ligands has been hampered in part by the limited number of methods available for the preparation of derivatives suitable as ligands.

SUMMARY OF THE INVENTION

The process of this invention comprises coupling a ketone with a 1,10-phenanthroline and a metal coupling reagent to provide a 2-[(1-hydroxy-substituted-alkyl)]-1,10-phenanthroline represented by the following Formula

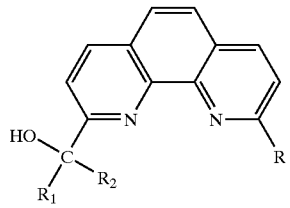

wherein
R is hydrogen, alkyl, alkyl substituted by one or two cycloalkyl or cycloalkenyl groups, cycloalkyl, cycloalkenyl, aryl, heterocyclic, bicycloalkyl or bicycloalkenyl;

$R_1$ and $R_2$ when taken separately, independently are alkyl, alkyl substituted by one or two cycloalkyl or cycloalkenyl groups, cycloalkyl, cycloalkenyl, bicycloalkyl or bicycloalkenyl, and when taken together with the carbon to which they are bonded are cycloalkyl, cycloalkenyl, bicycloalkyl or bicycloalkenyl; and wherein said R, $R_1$ and $R_2$ alkyl, cycloalkyl, cycloalkenyl, bicycloalkyl and bicycloalkenyl groups optionally bear substituents such as hydroxy, sulfhydryl, lower alkoxy, carboxy, phosphono, amino and like coordinating groups.

The term, "1-hydroxy-substituted-alkyl", refers to the 1-hydroxy group attached to the carbon bearing the $R_1$ and $R_2$ radicals as defined above and whether they are taken together or separately.

According to the process a 1,10-phenanthroline represented by the Formula 2

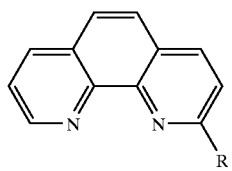

wherein R has the same meanings as defined for Formula 1 is mixed in an inert moderately polar solvent at a temperature between about 0° C. and about 75° C. with the ketone $R_1C(O)R_2$ wherein $R_1$ and $R_2$ have the above defined meanings, and a metal reagent to provide the compound represented by the Formula 1.

The products of the process represented by Formula 1 can be converted to a variety of other ligands by forming derivatives such as ethers and esters of the 1-hydroxy-substituted-alkyl substituent. The ligands obtained can form complexes with transition metals and the complexes can serve as catalysts in many processes, for example, in substitution and addition reactions and in the polymerization of monomers. In particular, the ligands provided by the process of the invention can be obtained in chiral form or converted to a chiral derivative for use in preparing chiral metal complexes. Such chiral complexes are useful in processes for the preparation of products in desired asymmetric forms.

In a further aspect the invention provides a 1,10-phenanthroline ligand represented by the following structural Formula 3.

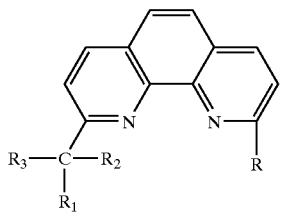

wherein R, $R_1$, and $R_2$ have the same meanings as defined herein above and $R_3$ is hydrogen, hydroxy, or a derivative of hydroxy such as an ether, ester, or a sulfhydryl, thioether, amino or amide group.

DETAILED DESCRIPTION

The coupling of a ketone with 1,10-phenanthroline according to the process of this invention can be regarded as a pinacol-like reaction. Although without being bound to any particular reaction mechanism, it appears that the process proceeds initially via a bimolecular reduction of the ketone mediated by a metal coupling reagent. It is also possible that a free radical mechanism may be involved.

Metal coupling reagents include, for example, magnesium, titanium, vanadium, manganese, copper, nickel, zinc, tin, lanthanides, and actinides and amalgams such as manganese and zinc amalgams. A preferred metal reagent for use in the process is a lanthanide II such as samarium. Samarium diiodide, diacetate or the triflate are useful coupling agents.

Solvents useful in the process are inert, moderately polar solvents which do not react with the metal reagent or the ketone employed. Such solvents include the ethers, for example, dialkyl ethers such as diethyl ether, methyl ethyl ether and the like, cyclic ethers such as tetrahydrofuran, dioxane, tetrahydropyran and the like, and diethers such as 1,2-dimethoxyethane and like ethers; esters such as methyl or ethyl acetate; and amides such as dimethylacetamide or phosphoramides. The choice of solvent will mainly be determined by the ease with which the product can be isolated from the reaction product mixture. Preferably the more volatile solvents are used.

The process can be carried out at a temperature between about 0° C. and about 75° C. and in many cases proceeds readily at or about 25° C. The rate at which the process proceeds varies with reagents and reactants and in general is complete in between about 4 and about 12 hours. The course of the reaction can be followed conveniently by thin layer chromatography. The ketone and metal reagent are used in amounts corresponding up to about 2.5 equivalent of the amount of 1,10-phenanthroline used. The reverse order of addition may be used and the reaction mixture is agitated during the process by stirring, shaking, or sonication.

The starting material, represented by the Formula 2, is obtained by known methods. For example, R substituents can be prepared by alkylation of the 1,10-phenanthroline with an alkyl, cycloalkyl or bicycloalkyl lithium compound. Many R alkyl, substituted alkyl, cycloalkyl and bicycloalkyl substituents also can be obtained, as described hereinafter, by first preparing a 1-hydroxy-substituted coupling product (Formula 1 wherein R is hydrogen) by the process of the invention and then forming a reducible derivative of the 1-hydroxy group. The derivative is subjected to reducing conditions to effect replacement of the reducible group with a hydrogen atom.

The group R (Formula 2) can be hydrogen or a straight or branched chained hydrocarbon group having from 1 to 12 carbon atoms, a cycloalkyl or cycloalkenyl group having from 4 to 10 ring carbon atoms, a mono- or dicycloalkyl substituted alkyl, a mono- or dicycloalkenyl substituted alkyl group wherein said cycloalkyl and cycloalkenyl have from 4 to 10 ring carbon atoms, an aryl or heterocyclic group, or a bicycloalkyl or bicycloalkenyl group having from 6 to 12 carbon atoms in the bicyclo ring. Examples of such R groups include methyl, ethyl, pentyl, iso-pentyl, iso-propyl, n-heptyl, cyclohexyl, cyclopentyl, cyclooctyl, cyclohexenyl, cyclopentenyl, cycloheptenyl, 4-cyclohexylbut-2-yl, 1-cyclohexenylethyl, or 1,3-dicyclopentylprop-2-yl; a dicycloalkylmethyl such as dicyclohexylmethyl, dicycloheptylmethyl, 1,3-dicyclopentylpropyl cyclohexylcyclohexenylmethyl, or cyclopentylcyclohexenylmethyl, an aryl or heterocyclic group such as phenyl, naphthyl or pyridyl, or a bicycloalkyl or bicycloalkenyl group which can be substituted by one or more alkyl groups, for example, a bicyclohexyl or bicycloheptyl group such as the 1-isopropyl-4-methylbicyclo[3.1.0]hex-3-yl group, the 1,7,7-trimethylbicyclo[2.2.1]hept-2-yl group, the 1,7,7-trimethylbicyclo[2.2.1]hept-2-ene-2-yl group and the 6,6-dimethylbicyclo[3.1.1]hept-2-ene-2-yl group. The R groups can be substituted with coordinating groups such as the hydroxy, sulfhydryl, amino, acyl, acetal and carboxy groups.

The ketone employed in the process is represented by the formula $R_1C(O)R_2$ wherein $R_1$ and $R_1$ and $R_2$ when taken separately are independently a straight or branched hydrocarbon radical having from 1 to 12 carbon atoms, a mono- or dicycloalkyl or a mono- or dicycloalkenyl-substituted alkyl group, a cycloalkyl or cycloalkenyl group, a bicycloalkyl or bicycloalkenyl group wherein said cycloalkyl and cycloalkenyl groups have from 4 to 10 carbon atoms and wherein said bicycloalkyl and bicycloalkenyl groups have from 6 to 12 carbon atoms. Examples or ketones which can be used in the process include acetone, methyl ethyl ketone, ethyl 2-carboxyethyl ketone, n-propyl 3-aminobutyl ketone, methyl-n-propyl ketone, methyl 3-hydroxypropyl ketone, methyl iso-propyl ketone, ethyl iso-butyl ketone, ethyl 4-mercaptobutyl ketone, methyl cyclopentyl ketone, ethyl cyclohexyl ketone, dodecyl methyl ketone, 2-(cyclohexylethyl)methyl ketone, di-[2-(cyclohex-3-ene)ethyl]ketone, dicyclohexyl ketone, dicyclopentyl ketone, cyclohexyl-4-aminocyclohexyl ketone, cyclopentyl cyclohexyl ketone, cyclopentyl 3-carboxycyclohexyl ketone, cyclohexanone, cyclopentanone, 3-hydroxycyclohexanone, menthone, cycloheptanone, cyclooctanone, cyclononanone, camphor, thujone, nopinone, bicycloheptanone, bicyclooctanone, and like alkyl, cycloalkyl and bicycloalkyl ketones.

In carrying out the process with a substituted ketone wherein the substituent is, e.g., a carboxy, hydroxy, sulhydryl or amino substituent, the substituent can be in protected form to minimize any untoward side reactions. Protecting groups generally employed for the temporary protection or blocking of such substitutents and which are unreactive under the conditions of the process can be used. For example, the carboxy group may be protected with a benzyl ester group, the hydroxy and sulfhydryl groups may be protected as an ether such as a silyl ether or an allyl or benzyl ether, and the amino group may be protected with an alkyloxycarbonyl group such as the t-butyloxycarbonyl group. Following the process the protected 1-hydroxy-substituted-alkyl product is deprotected to provide the desired coupling product.

The following Table 1 lists the percent yield of the 1-hydroxy-substituted-alkyl coupling products obtained in the process with the listed ketones and 1,10-phenanthroline. (Formula 2, R=H)

TABLE I

| Ketone | Percent Yield 1-Hydroxy coupling. Product |
| --- | --- |
| Cyclohexanone | 88 |
| Diethyl ketone | 89 |
| Methyl ethyl ketone | 73 |
| Methyl iso-propyl ketone | 71 |
| Methyl-t-butyl ketone | 40 |
| Thujone | 45 |
| Menthone* | 54 |

*Racemic menthone was used.

The foregoing description of the ketones that can be employed in the process is not intended to be limiting. Those skilled in the art will appreciate that ketones other than those described also will be useful in the process.

Based on the pinacol-like coupling reaction of the process it is likely that other reagents can be used in the process with some modifications of reaction conditions. For example, the process may be useful in the coupling of aromatic ketones, aldehydes, imines, nitrites, acyl compounds and epoxides.

An embodiment of the process comprises mixing a stirred solution of 1,10-phenanthroline in tetrahydrofuran (THF) with a solution of the lanthanideII, samarium diiodide, in THF at a temperature of about 25° C. To the mixed solutions is added a solution of the ketone, methyl ethyl ketone, and the reaction mixture is stirred at about 25° C. for about 12 hours. The reaction is then quenched by the addition of a saturated aqueous solution of ammonium chloride and the mixture extracted with methylene chloride. The extract is washed with brine, dried and concentrated in vacao. The concentrate of product is purified by flash chromatography using alumina and ethyl acetate-hexanes as a gradient to provide racemic 2-[(1-hydroxy-1-methylpropyl)]-1,10-phenanthroline. (Formula 1, R=H, R$_1$=ethyl, R$_2$=methyl) This embodiment is depicted in the following reaction scheme wherein MEK is methyl ethyl ketone.

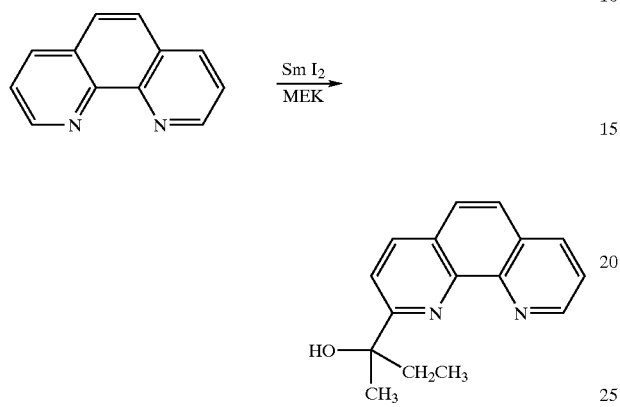

Another embodiment of the process comprises mixing a solution of 1,10-phenanthroline in THF with a solution of samarium diiodide in THF and adding to the mixed solutions a solution of the chiral bicyclic ketone, (−)-thujone, in THF. The chiral product, 2-{(1S,3R,4S,5R)-(3-hydroxy-1-isopropyl-4-methylbicyclo[3.1.0]hex-3-yl)}-1,10-phenanthroline, is isolated and purified as described above in the preceding embodiment. This embodiment is illustrated by the following reaction scheme.

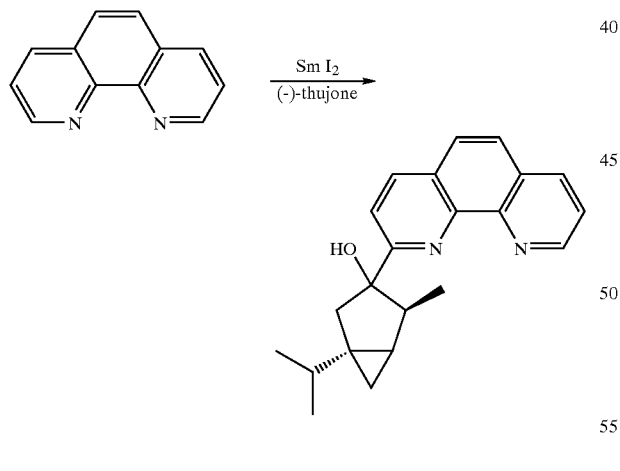

In a further embodiment of the invention, a solution of 2-(cyclohexyl)-1,10-phenanthroline and samarium diiodide is treated with a solution of cyclohexanone in THF. Following completion of the reaction the product is recovered from the reaction mixture by extraction and is purified by chromatography to provide 2-[(cyclohexyl)-9-(1-hydroxycyclohexyl)]-1,10-phenanthroline. (Formula 1, R=cyclohexyl, R$_1$ and R$_2$ taken together=cyclohexyl. The reaction scheme below illustrates the embodiment.

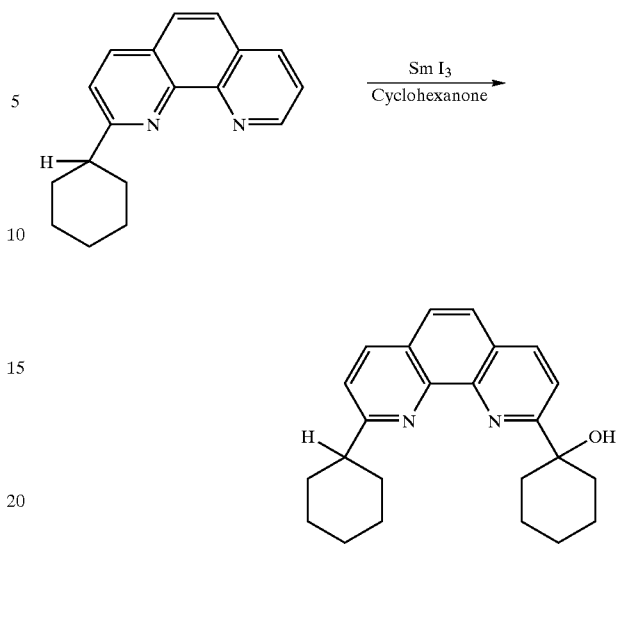

Certain starting materials are preferred in the process of the invention. Preferred starting materials represented by the Formula 2 wherein R is a chiral ar an achiral substitutent. Preferably, the ketone employed is a chiral ketone or a prochiral ketone i.e., one that when employed produces a phenanthroline in racemic form that is readily resolved by standard methods.

Some α,β-unsaturated ketones do not appear to react in the same manner as saturated ketones under the current process conditions. For example, in the case of the reaction of the ketone pulegone with 1,10-phenanthroline, conjugate addition of the 2-position of the phenanthroline ring occurs along with reduction of the substituted pyridine ring to form a compound represented by the formula.

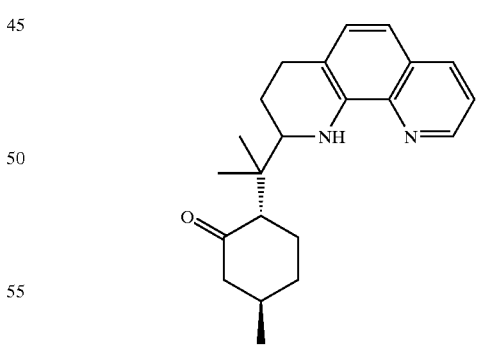

Although the desired 1-hydroxy-substituted-alkyl coupling product is not obtained the product is nevertheless useful. For example, the product can be dehydrogenated with dichlorodicyanoquinone (DDQ) or other aromatizing reagent to provide the 2-substituted-1,10-phenanthroline represented by the following formula.

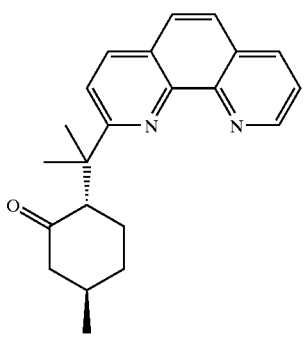

The keto group of the aromatized product can be reduced to the hydroxy group and the latter, if desired, derivatized to form other ligands.

As was noted herein above the 1-hydroxy coupling products of the process also are useful intermediates for reduction to the corresponding alkyl, cycloalkyl and bicycloalkyl substituted phenanthroline. For example, a 2-[(1-hydroxy-substituted-alkyl)]-1,10-phenanthroline is converted to the corresponding 2-alkoxy derivative via alkylation with an alkyl halide and a base such as sodium hydride. The 1-alkoxy group is readily removed by reduction to provide the 2-alkyl, 2-cycloalkyl or 2-bicycloalkyl phenanthroline. The reduction of the 1-alkoxy group can be carried out with a number of known reducing agents owing to the benzylic character of the 1-alkoxy group in the 2-position of the aromatic phenanthroline ring to which it is attached. Reduction methods such as hydrogenolysis with a metal catalyst such as palladium, and chemical reductions carried out with reducing agents such as an alkali metal, for example, sodium or lithium, chromiumII reagents, or with lanthanideII reagents such as samarium diiodide are applicable methods. The reduction method chosen should be one that will not cause any substantial reduction of the phenanthroline moiety. Other derivatives of the 1-hydroxy group such as an ester, a thioether, or a halo derivative can be reduced.

The alkoxylation and reduction reactions are illustrated by the following reaction scheme

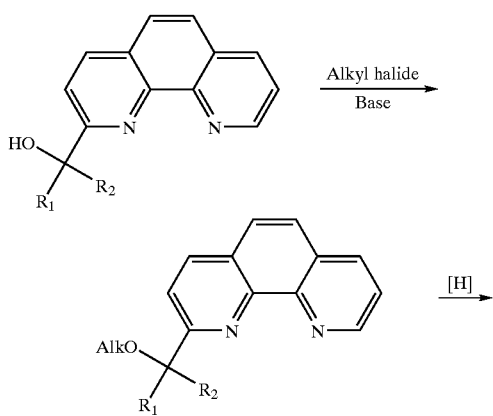

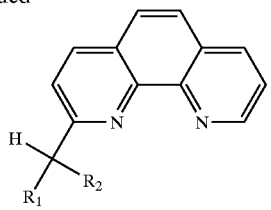

An embodiment of the above described 2-step process is shown in the following reaction scheme wherein R is hydrogen and 2-[(1-hydroxy-1-methylpropyl)]-1,10-phenanthroline is prepared by coupling methyl ethyl ketone with 1,10-phenanthroline, and the coupling product alkylated with methyl iodide and sodium hydride to form 2-[(1-methoxy-1-methylpropyl)]-1,10-phenanthroline. The latter is reduced with the lanthanideII reducing agent, samarium diiodide, to provide 2-(1-methylpropyl)-1,10-phenanthroline.

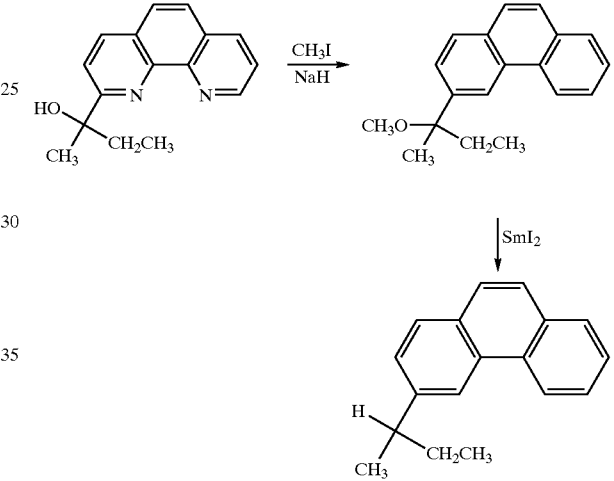

Table 2 lists the percent yields obtained with representative 2-(1-alkoxy-substituted-alkyl)-1,10-phenanthrolines and their reduction products.

TABLE 2

| 2-[(1-Hydroxy-substituted alkyl)]1-,10-Phenanthroline | Percent Yield | |
|---|---|---|
| | Methyl Ether | Reduction Product |
| 1-hydroxycyclohexyl | 90 | 66 |
| 1-hydroxy-1-ethylpropyl | 66 | — |
| 1-hydroxy-1-methylpropyl | 72 | 45 |
| 1-hydroxy-1,2-dimethyl-propyl | 70 | 58 |
| 1-hydroxy-1,2,2-trimethyl-propyl | 55 | — |
| (1S, 3R, 4S, 5R)-3-hydroxy-1-isopropyl-4-methylbicyclo-[3.1.0]hex-3-yl[1] | 75 | 68 |
| (2R*, 5S*)-1-hydroxy-2-isopropyl-5-methylcyclohexyl[2] | 88 | — |

[1] Obtained with (-)-thujone
[2] Obtained with racemic menthone
A dash indicates not determined The reduction product then can be used as a substrate in the coupling process of the invention to provide a compound represented by the Formula 1 as shown in the following reaction wherein a lanthanideII is the metallic coupling reagent.

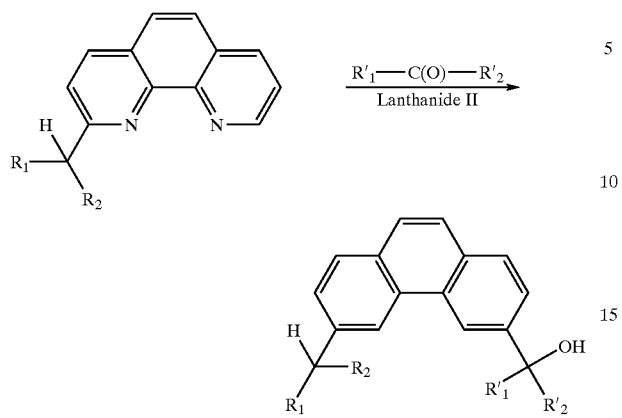

In the above reaction scheme the R'$_1$ and R'$_2$ groups have the same meanings as defined above for R$_1$ and R$_2$ and the R'$_1$ and R'$_2$ groups of the R'$_1$R'$_2$ C(OH)— group and R$_1$ and R$_2$ groups of the the R$_1$R$_2$CH— reduced group can differ from each other to provide one or more racemates which can be resolved by standard methods. Also, the R'$_1$ and R'$_2$ groups of the starting material and the R$_1$ and R$_2$ groups of the coupling product can contain substituents with one or more asymmetric centers as discrete isomers which are not subject to racemization in the process steps.

The hydroxy group of the 1-hydroxy-substituted-ligands represented by the Formula 1 forms derivatives which are useful in the preparation of a variety of ligands or metal-coordinating groups. The derivatives can be obtained either by replacement of the hydroxy group e.g., by a sulfhydryl group or an amino group, both of which may be derivatized or by substitution of the hydrogen of the hydroxy group with another group such as alkyl or acyl. These derivatives can be tailored for use in forming metal complexes which catalyze specific reactions. The 1-hydroxy group thus provides a convenient handle for the preparation of a number of additional ligands which can contain centers of asymmetry useful in promoting asymmetric reactions.

As described herein above, the invention also provides 1,10-phenanthroline compounds represented by the Formula 3, Formula 3

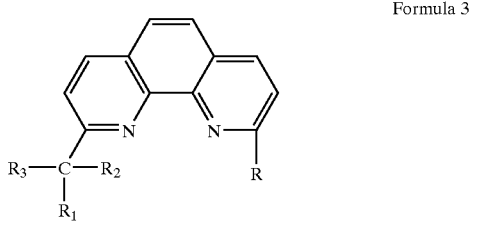

wherein R, R$_1$ and R$_2$ have the same meanings as defined above in Formulas 1 and 2 and R$_3$ represents hydrogen, hydroxy, sulfhydryl (HS-), amino, chloro, bromo or, a derivative of the hydroxy, sulfhydryl, or amino group, preferably one that contains metal-coordinating groups that promote asymmetric reactions. Particular derivatives of the hydroxy, sulfhydryl and amino groups which can be obtained by well-known reactions are those defined below: wherein R$_3$ is a group of the formulas, (a) an acyl group, R$_4$—Z—C(O)-y-, (b) an ether group, R$_4$—Z-y-, (c) a sulfinyl or sulfonyl group, R$_4$—Z—S(=O)$_x$—, (d) an amide group, R$_4$—Z—C(O)N(R$_6$)—, (e) an amino group, R$_4$—Z—N(R$_6$)—

(f) an imine group, R$_4$—Z—CH=N—.

wherein y is O or S;

x is 1 or 2;

Z is a divalent hydrocarbon radical, —[CH(R$_5$)—CH$_2$]$_m$— a divalent alkene radical, —[CH=C(R$_5$)]$_m$—, or a divalent alkyl polyether radical, —[CH$_2$OCH$_2$—[CH(R$_5$)]$_n$—O—CH$_2$]$_m$—, wherein $_m$ and $_n$ are 0 or an integer of from 1 to 4;

R$_4$ and R$_5$ independently are hydrogen, C$_1$-C$_{10}$ alkyl, C$_2$-C$_{10}$ alkenyl, C$_2$-C$_{10}$ alkynyl; a 5- or 6-membered heterocyclic ring containing one or more of the same or different nitrogen, oxygen or sulfur ring atoms and wherein said heterocyclic ring can be a benzheterocycle; phenyl, substituted phenyl, benzyl, substituted benzyl; C$_1$-C$_6$ perfluoroalkyl; a di- to hexapeptide; a mono- or disaccharide; and said C$_1$-C$_{10}$ alkyl, C$_2$-C$_{10}$ alkenyl, C$_2$-C$_{10}$ alkynyl substituted by hydroxy, amino, sulfhydryl, lower alkylcarbonyl, lower alkoxy, lower alkylthio, sulfo, lower alkylsufonyl, lower alkylsulfinyl, carboxy, lower alkoxycarbonyl, acyl, acyloxy, a lower alkyl acetal of the formula, —CH(O-lower alkyl)$_2$, aminocarbonyl, (mono- or di-lower alkyl) aminocarbonyl, C$_2$-C$_5$ alkenyl, C$_4$-C$_8$ dienyl, cyclopentadienyl, cyclohexadienyl, C$_2$-C$_8$ alkynyl, a 5- or 6-membered heterocyclic ring as defined above and wherein said heterocycle can be a benzoheterocycle, phosphino, phosphono, C$_1$-C$_6$ perfluoroalkyl, phenyl, substituted phenyl, benzyl, substituted benzyl, a di- to hexapeptide, a monosaccharide or a disaccharide substituent; and R$_6$ is hydrogen or lower alkyl.

The term Z represents a linking group which can be used to link the R$_4$ group with, for example, the 1-hydroxy, or sulfhydryl group of the 1,10-phenanthroline parent compound. The linking group itself, as well as the R$_4$ group, can contain substitutents as defined above to provide a variety of groups capable of metal coordination.

The term, "lower alkyl", as used herein represents a C$_1$-C$_6$ alkyl group which can be a straight or branched chain hydrocarbon group such as, for example, methyl, ethyl, n-propyl, iso-propyl, n-butyl, iso-butyl, t-butyl, n-pentyl, iso-pentyl, neo-pentyl, n-hexyl and the like. Such lower alkyl groups may contain unsaturation and may be further substituted by substituents such as hydroxy, sulfhydryl, amino, phosphino, an acetal group, carboxylate, ester, ether, alkanoyl, or aroyl.

The terms, "substituted phenyl" and "substituted benzyl", refer to phenyl and benzyl substituted by one or two of the same or different alkyl, alkenyl, hydroxy, amino, mono- or di-lower alkylamino, lower alkoxy, lower alkylthio, sulfo, lower alkylsulfinyl, lower alkylsulfonyl, carboxy, lower alkoxycarbonyl, acyl, acyloxy, aminocarbonyl, (mono- or di-lower alkyl)aminocarbonyl, phosphino, phosphono, a lower alkyl acetal of the formula, —CH(O-lower alkyl)$_2$, C$_1$-C$_8$ perfluoroalkyl, a di- to hexapeptide, a monosaccharide or a disaccharide substitutent.

Examples of R$_4$C(O) acyl groups (a) and R$_5$C(O) acyl groups include formyl, acetyl, propionyl, butyryl, hexanoyl, decanoyl, 2-hydroxyacetyl, 3-hydroxypropyl, 4-mercaptobutyryl, ω-hydroxyoctanoyl, ω-mercaptoheptanoyl; an amino substituted acyl group e.g. derived from an amino acid such as glycine, alanine, methionine, histidine, glutamine, proline, phenylglycine and aspartic acid; acyl groups derived from malonic acid, mandelic acid, lactic acid, benzoic acid, 4-aminobenzoic acid, phenylacetic acid, 3-methoxyphenylacetic acid, crotonic acid, 4-propargylbenzoic acid, 2-allylbenzoic acid, 4-carboxybutyric acid, 3-allylbutyric acid, heterocyclic acids such as thiophene-2-carboxylic acid, furan-2-carboxylic acid, benzothienyl-2-carboxylic acid, pyridine-2-carboxylic acid, nicotinic acid, 2-thienylacetic acid, and like acids.

When in the Formula 3, $R_4$ is an ether group (b), or $R_5$ is an ether group, examples of such groups include methoxy, methylthio, ethoxy, iso-propoxy, n-butoxy, allyloxy, propargyloxy, hexyloxy, 6-hydroxyhexyloxy, 5-carboxypentyloxy, benzyloxy, 4-aminobenzyloxy, 3-(2-phosphinophenyl)propoly, 3-(2-methylthiophenyl)propoxy, 2-mercaptobenzyloxy, 3-allylbutoxy, 4-hydroxybutyloxy, 3-mercaptopropyloxy, 3,5-dimercaptopentyloxy, 4-methylsulfonylbutoxy, 2-cyclopentadienylethoxy, and like ethers.

When $R_4$ or $R_5$ is a carbohydrate examples of such carbohydrates include the mono- and disaccharides such as glucose, sucrose, maltose, mannose, lactose, inositol, ascorbic acid, sorbitol, cellobiose, and like carbohydrates.

Heterocyclic substitutents of $R_4$ or $R_5$ include, for example, thiophene, benzothiophene, benzofuran, furan, thiadiazole, oxadiazole, pyridine, pyrrole, piperdine, pyrrolidine, quinoline, imidazole, 1H-tetrazole, pyran, pyrimidine, thiazine, oxazole, oxazoline, pyrazine, triazine, benzoxazole, thiazole, benzthiazole and indole.

Perfluoroalkyl groups are exemplified by trifluoromethyl, pentofluoroethyl and the like.

Examples of peptide substituents of $R_4$ or $R_5$ include e.g., Met-Ala-Glycyl, Pro-Leu-Leu-Alanyl, His-Gly-Leu-Pro-Glycyl, and like peptides.

Examples of olefinic groups represented by $R_4$ or $R_5$ include e.g., vinyl, allyl, butenyl, iso-pentenyl, deca-6,9-dienyl, nonenyl, and 8-hydroxyoct-3-enyl.

The compounds represented by the Formula 3 wherein $R_3$ is sulfhydryl can be obtained by reacting the chloro or bromo derivatives of the 1-hydroxy group ($R_3$=Cl or Br) with an alkali metal salt of hydrogen sulfide. The chloro and bromo derivatives of the 1-hydroxy group can be obtained by reacting the 1-hydroxy group with concentrated hydrochloric and hydrobromic acids. Ethers are prepared by the alkylation of the hydroxy or sulhydryl group with e.g., an alkyl or olefinic bromide. Ester groups, $R_4$—Z—C(O)-y- and amide groups $R_4$—Z—C(O)N($R_6$)— are prepared by the acylation of the hydroxy, sulfhydryl and amino groups respectively. For example, the hydroxy group may be reacted with an active derivative of the carboxy group of the acid $R_4$—Z—COOH, such as an acid chloride, an acid anhydride, or an azide, to form the ester. Amino derivatives can be obtained by Ritter-type reactions in which the hydroxy derivatives undergo reactions with nitrites, trialkyl-silyl cyanides, or corresponding reagents in the presence of acid catalysts or other promoters to form initially amides or correspomding derivatives which can be converted to the desired amino derivatives by hydrolysis or other appropriate reactions. Amides can be obtained by reaction of the acid halide with the amino derivative HN($R_6$)—. Imines can be prepared by the reaction of the amino derivative ($R_3$=NH$_2$) with the aldehyde $R_4$—Z—CHO with appropriate means to remove the water liberated during the reaction. The sulfinyl and sulfonyl derivatives of the group (c) above can be obtained by the oxidation of groups (a) and (b), wherein y is sulfur, with a peracid such as peracetic acid or perbenzoic acid. Those in the art will appreciate that the derivatives described herein can be obtained in reactions other than those illustrated above.

Among the compounds represented by the Formula 3 the 1-hydroxy compounds ($R_3$=OH) and the acyl and ether derivatives thereof are preferred. Further preferred are the 1-hydroxy compounds wherein the linking group Z is absent ($R_4$—Z—C(O)—, m=0). Also preferred are compounds wherein $R_4$ is an alkyl, alkenyl, alkynyl or aryl group substituted by hydroxy, sulfhydryl, amino, carboxy, formyl or an acetal group [—CH(—O-lower alkyl)$_2$]. Other preferred compounds represented by Formula 3 are the sulfydryl derivatives of the hydroxy group ($R_3$—SH) and the acyl and ether derivatives thereof.

The 1,10-phenanthioline ligands provided by the process and the ligand derivatives thereof can form complexes with transition metals in general. These complexes are useful inter alia, in catalytic reactions such as addition reactions, substitution reactions, in directing the topography of polymers during catalytic polymerizations of ethylene or propylene, selective DNA cleavages, reagents for chemical analysis of metals and in the preparation of pharmaceuticals in asymmetric forms. The metal-ligand complexes are represented by the following formula,

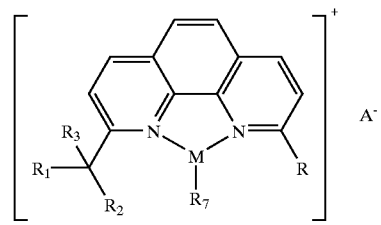

wherein R, $R_1$, $R_2$, and $R_3$ are as defined herein and $R_7$ is e.g., a bound reacting group such as allyl, alkenyl, or aryl and A is a counter ion. Examples of complexes which may be prepared are described by P.-O. Norrby, P. Helquist, J. D. Oslob, and B. Akermark, "Quantitative Structure-Reactivity Relationships in Palladium-Catalyzed Allylation Derived From Molecular Mechanics (MM2) Calculations", *Organometallics* 1997, 16, 3015–3021.

The phenanthroline ligand-metal complexes formed with the ligands provided herein also can be resolved after formation if desired, e.g. when a ligand of the invention is an achiral ligand.

EXAMPLES

The following examples are provided to further illustrate the processes and the preparation of ligands described herein and are not to be construed as limitations thereof. In the examples, the following terms have the designated meanings:

THF is tetrahydrofuran

HRMS is High Resolution Mass Spectrum

NOE is Nuclear Overhauser Effect

TLC is Thin Layer Chromatography

Proton ($^1$H) nuclear magnetic resonance spectra were obtained with a General Electric GN-300 (300 MH$_z$) spectrometer. Carbon ($^{13}$C) NMR spectra were obtained with the General Electric spectrometer at 75 MH$_z$. Infrared spectra were recorded on a Perkin-Elmer Model 1420 spectrophotometer. Mass spectral data were obtained on a Finnigan MAT 8430 spectrometer. HRMS data were obtained by electron impact. Optical rotations were determined with a Rudolph Research Autopol III polarimeter at 546 nm.

The protons of the phenanthroline ring are designated in the NMR spectra by $H_p$ as shown in the following formula.

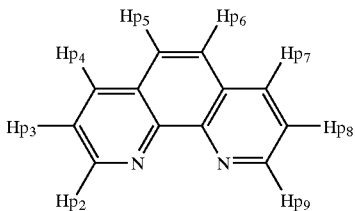

General Procedure I

General Procedure for Samarium Diiodide Mediation of Addition of Carbonyl Compounds to 1,10-Phenanthroline To a stirred solution of 1,10-phenanthroline (0.1 g, 0.55 mmol) in THF (5 mL) was added a 0.1 M solution of $SmI_2$ in THF (12.2 mL, 1.22 mmol) at 25° C. After being stirred for 5 min, the carbonyl compound (1.22 mmol) was added, and the resulting mixture was stirred for 12 h at 25° C. and was monitored by TLC. Upon completion of the reaction, a saturated solution of $NH_4Cl$ was added to quench the reaction, and the resulting mixture was extracted with $CH_2Cl_2$. The organic extracts were combined, washed with brine, dried over $MgSO_4$, filtered and concentrated. The product was purified by flash chromatography (alumina, ethyl acetate/hexanes gradient).

Example 1

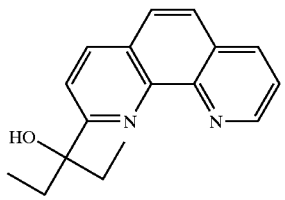

2-[(1-Hydroxycyclohexyl)]-1,10-phenanthroline

Through use of the above general procedure, cyclohexanone (0.120 g, 1.22 mmol) was converted into 0.134 g (88% yield) of the title compound as a colorless oil: $^1H$ NMR (300 MHz, $CDCl_3$) δ9.18 (dd, J=4.20, 1.80 Hz, $H_{p9}$), 8.28 (dd, J=8.40 Hz, $H_{p4}$), 8.27 (dd, J=8.40, 1.80 Hz, $H_{p7}$), 7.82 and 7.79 (two d, J=8.80 Hz, $H_{p5}$ and $H_{p6}$), 7.76 (d, J=8.40 Hz, $H_{p3}$), 7.65 (dd, J=8.10, 4.50 Hz, $H_{p8}$), 2.08–1.7 (m, 10H, cyclohexyl); $^{13}C$ NMR (75 MHz) δ166.52, 150.31, 145.81, 143.96, 137.15, 136.06, 129.00, 127.46, 126.28, 126.20, 122.93, 119.21, 73.50, 38.63, 23.70, 22.15; IR ($CHCl_3$) 3352 (OH), 3048 (C—H Ar), 2928 (CH), 909 (C—H Ar) $cm^{-1}$; HRMS m/e Calcd for $C_{18}H_{19}N_2O$ ($MH^+$): 279.1497. Found: 279.1490.

Example 2

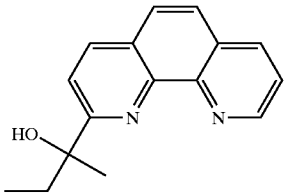

2-[(1-Ethyl-1-hydroxypropyl)]-1,10-phenanthroline

Through the use of the general procedure, 3-pentanone (0.105 g, 1.22 mmol) was converted to 0.132 g (89% yield) of the title compound as a colorless oil: $^1H$ NMR (300 MHz, $CDCl_3$) δ9.21 (dd, J=4.50, 1.80 Hz, $H_{p9}$), 8.26 (one d, J=8.40 Hz, $H_{p4}$, one dd, J=8.40, 1.80 Hz, $H_{p7}$), 7.82 and 7.79 (two d, J=8.80 Hz, $H_{p5}$ and $H_{p6}$), 7.64 (dd, J=8.10, 4.20 Hz, $H_{p8}$), 7.61 (d, J=8.40 Hz, $H_{p3}$), 2.01 (dq, J=7.50, 2.10 Hz, $CH(CH_2CH_3)_2$), 0.77 (t, J=7.20 Hz, $CH(CH_2CH_3)_2$); $^{13}C$ NMR (75 MHz) δ164.10, 150.14, 145.52, 143.67, 136.96, 136.24, 128.99, 127.25, 126.22, 122.92, 119.49, 77.27, 34.69, 7.98; IR ($CHCl_3$) 3417 (OH), 2967 (C—H Ar), 2929 (CH), 912 (C—H Ar) $cm^{-1}$; HRMS m/e Calcd for $C_{17}H_{19}N_2O$ ($MH^+$): 267.1497. Found: 267.1497.

Example 3

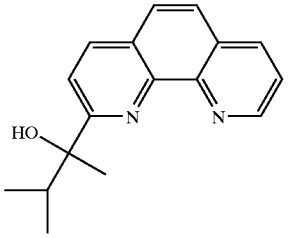

2-[(1-Hydroxy-1-methylpropyl)]-1,10-phenanthroline

Through the use of the above general procedure, 2-butanone (0.088 g. 1.22 mmol) was converted to 0.101 g (73% yield) of the title compound as a colorless oil: 1H NMR (300 MHz, $CDCl_3$) δ9.20 (dd, J=4.50, 1.80 Hz, $H_{p9}$), 8.28 (d, J=8.40 Hz, $H_{p4}$), 8.28 (dd, J=8.10, 1.80 Hz, $H_{p7}$), 7.28 and 7.79 (two d, J=8.80 Hz, $H_{p5}$ and $H_{p6}$), 7.67 (d, J=8.40 Hz, $H_{p3}$), 7.65 (dd, J=8.10, 4.20 Hz, $H_8$), 2.02 (two dq, J=13.5, 5.4 Hz, $CH_2CH_3$), 1.67 (s, $C(OH)CH_3$), 0.82 (t, J=7.35 Hz, $CH_2CH_3$); $^{13}C$ NMR (75 MHz) δ165.41, 150.23, 145.63, 143.74, 137.14, 136.18, 129.02, 127.34, 126.29, 126.20, 122.95, 119.29, 74.64, 35.94, 29.17, 8.23.

Example 4

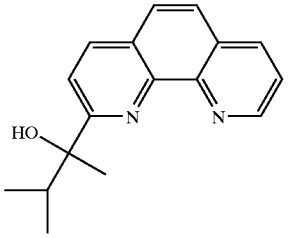

2-[(1-Hydroxy-1,2-dimethylpropyl)]-1,10-phenanthroline

By using the above general procedure, 3-methyl-2-butanone (0.105 g, 1.22 mmol) was converted to 0.105 g (71% yield) of the title compound as a colorless oil: ¹H NMR (300 MHz, CDCl₃) δ9.18 (dd, J=4.40, 1.80 Hz, H$_{p9}$), 8.26 (one d, J=8.10 Hz, H$_{p4}$, one dd, J=8.10, 1.80 Hz, H$_{p7}$), 7.82 and 7.78 (two d, J=8.80 Hz, H$_{p5}$ and H$_{p6}$), 7.65 (d, J=8.70 Hz, H$_{p3}$), 7.64 (dd, J=8.10, 4.50 Hz, H$_{p8}$), 6.10 (br s, OH), 2.19 (sep, J=6.60 Hz, CH(CH₃)₂), 1.64 (s, C(OH)CH₃), 1.12 (d, J=6.60 Hz, CH(CH₃)CH₃), 0.71 (d, J=6.60 Hz, CH(CH₃)CH₃); ¹³C NMR (75 MHz) δ165.84, 150.19, 145.70, 143.63, 136.87, 136.08, 129.00, 127.31, 126.24, 126.16, 122.89, 119.54, 76.29, 38.43, 26.43, 17.46, 17.09.

Example 5

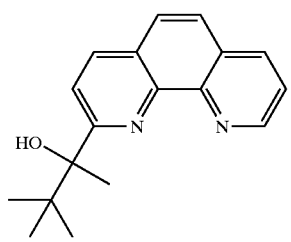

2-[(1-Hydroxy-1,2,2-trimethylpropyl)]-1,10-phenanthroline

By following the above general procedure, 3,3-dimethyl-2-butanone (0.122 g, 1.22 mmol) was converted to 0.061 g (40% yield) of the title compound as a colorless oil: ¹H NMR (300 MHz, CDCl₃) δ9.17 (dd, J=4.20, 1.80 Hz, H$_{p9}$), 8.26 (dd, J=8.40, 1.50 Hz, H$_{p7}$), 8.23 (d, J=8.40 Hz, H$_{p4}$), 7.82 and 7.78 (two d, J=8.80 Hz, H$_{p5}$ and H$_{p6}$), 7.70 (d, J=8.40 Hz, H$_{p3}$), 7.63 (dd, J=8.10, 4.50 Hz, H$_{p8}$), 1.71 (s, CH₃), 1.02 (s, (CH₃)₃); ¹³C NMR (75 MHz) δ164.19, 150.13, 145.81, 143.32, 136.04, 135.73, 128.97, 127.23, 126.09, 122.91, 121.31, 78.19, 38.99, 26.08, 23.06.

Example 6

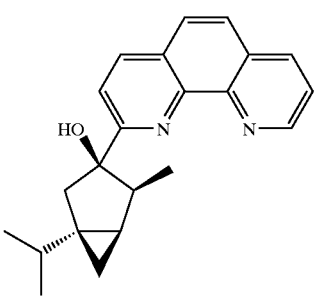

2-[(1S,3R,4S,5R)-(3-Hydroxy-1-isopropyl-4-methylbicyclo[3.1.0]hex-3-yl)]1,10-phenanthroline By using the general procedure above, (−)-thujone (0.186 g, 1.22 mmol) was reacted with 1,10-phenanthroline to provide 0.083 g (45% yield) of the title compound as a colorless oil: ¹H NMR (300 MHz, CDCl₃) δ9.16 (dd, J=4.50, 1.80 Hz, H$_{p9}$), 8.27 (d, J=8.40 Hz, H$_{p4}$), 8.24 (dd, J=8.10, 1.80 Hz, H$_{p7}$) 7.82 and 7.76 (two d, J=8.80 Hz, H$_{p5}$ and H$_{p6}$), 7.72 (d, J=8.40 Hz, H$_{p3}$), 7.62 (dd, J=8.10, 4.50 Hz, H$_{p8}$), 6.38 (br s, OH), 2.75 (dq, J=6.6, 4.5 Hz, CHCH₃), 2.50 (dd, J=13.5, 1.2 Hz, C(OH)CHH), 2.21 (d, J=13.5 Hz, C(OH)CHH), 1.53 (sep, 6.9 Hz, CH(CH₃)₂), 1.37 (t, J=3.9 Hz, cyclopropyl H), 1.31 (dd, J=4.2, 8.4 Hz, cyclopropyl H), 1.07 (d, J=6.9 Hz, CH₃), 0.95 (d, J=6.9 Hz, CH₃), 0.89 (d, J=6.9 Hz, CH₃), 0.37 (dd, J=4.5, 9.0 Hz, cyclopropyl H); ¹³C NMR (75 MHz) δ165.09, 150.16, 145.56, 142.86, 137.10, 136.05, 128.98, 127.17, 126.29, 126.05, 122.87, 119.72, 81.85, 48.66, 46.71, 33.01, 32.70, 29.53, 20.10, 19.94, 13.12, 11.60; IR (CHCl₃) 3381 (OH), 2957 (C—H Ar), 2928 (CH), 850 (C—H Ar) cm⁻¹; HRMS m/e Calcd for C₂₂H₂₅N₂O (MH⁺): 333.1967, found: 333.1943.

Example 7

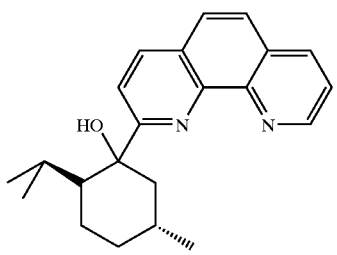

2-[(2R*,5S*)-1-Hydroxy-2-isopropyl-5-methylcyclohexyl)]-1,10-phenanthroline

By following the above general procedure, dl-menthone (0.186 g, 1.22 mmol) was reacted with 1,10-phenanthroline to provide 0.100 g (54% yield) the title compound as a colorless oil: ¹H NMR (300 MHz, CDCl₃) δ9.17 (dd, J=4.20, 1.80 Hz, H$_{p9}$), 8.26 (d, J=8.40 Hz, H$_{p4}$), 8.24 (dd, J=8.10, 1.80 Hz, H$_{p7}$), 7.82 and 7.78 (two d, J=8.80 Hz, H$_{p5}$ and H$_{p6}$), 7.68 (d, J=8.40 Hz, H$_{p3}$), 7.62 (dd, J=8.10, 4.50 Hz, H$_{p8}$), 2.12 (m, 1H), 1.94 (m, 2H), 1.84 (m, 2H), 1.71 (m, 2H), 1.42 (m,1H), 0.89 (m, 6H), 0.69 (d, J=6.60 Hz, 3H); ¹³C NMR (75 MHz) δ165.96, 150.22, 145.64, 143.73, 136.98, 135.98, 128.95, 127.26, 126.18, 126.12, 122.87, 119.18, 77.98, 50.96, 49.63, 35.35, 28.47, 27.82, 23.76, 22.39, 22.18, 18.84.

General Procedure II

General Procedure for Preparation of 2-(Alkoxyalkyl)-1,10-Phenanthrolines

To a stirred THF solution of 1 equivalent of the 2-(hydroxyalkyl)-1,10-phenanthroline obtained as described in the foregoing Examples is added in one portion NaH (4 equiv.) followed by ther addition of an alkyl iodide (4 equiv.). The mixture is stirred at a temperature of about 25° C. and monitored for progress of the reaction by TLC. After the reaction is completed, a saturated aqueous solution of NH₄Cl was added to quench the reaction. The resulting mixture is extracted with methylene chloride, the organic extracts combined, washed with brine, dried over magnesium sulfate, filtered and concentrated. The product is purified by flash chromatography over alumina gel using ethyl acetate/hexanes as a gradient.

Example 8

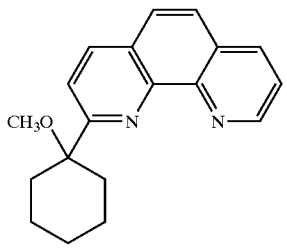

2-[(1-Methoxycyclohexyl)]-1,10-phenanthroline

Through use of General Procedure II, NaH (0.110 g 4.6 mmol), methyl iodide (0.65 mL, 4.6 mmol), and 2-[(1-hydroxycyclohexyl)]-1,10-phenanthroline (0.320 g, 1.15 mmol), prepared as described by Example 1, were reacted to provide 0.301 g (90% yield) of the title methyl ether as a colorless oil: $^1$H NMR (300 MHz, CDCl$_3$) δ9.24 (dd, J=4.50, 1.80 Hz, H$_{p9}$), 8.25 (d, J=8.40 Hz, H$_{p4}$, dd, J=8.10, 2.40 Hz, H$_{p7}$), 7.96 (d, J=8.40 Hz, H$_{p3}$), 7.82 and 7.75 (two d, J=8.80 Hz, H$_{p5}$ and H$_{p6}$), 7.61 (dd, J=8.10, 4.50 Hz, H$_{p8}$), 3.11 (s, 3H, OCH$_3$), 2.23 (m, 4H, cyclohexyl H), 1.74 (m, 6H, cyclohexyl H); $^{13}$C NMR (75 MHz) δ166.33, 150.49, 146.33, 145.11, 136.40, 136.04, 128.77, 127.41, 126.38, 126.03, 122.40, 120.45, 80.46, 50.45, 33.83, 25.08, 21.69; IR (CHCl$_3$) 3048 (C—H Ar), 2933 ((CH), 908 (C—H Ar), cm$^{-1}$; HRMS m/e Calcd for C$_{19}$H$_{21}$N$_2$O (MH$^+$): 293.1654, found: 293.1665.

Example 9

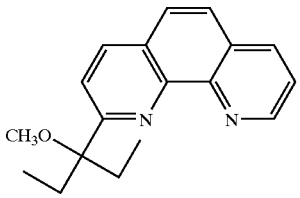

2-[(1-Ethyl-1-methoxypropyl)]-1,10-phenanthroline

By using General Procedure II, NaH (0.035 g, 1.5 mmol), methyl iodide (0.092 mL, 1.5 mmol), and 2-[(1-ethyl-1-hydroxypropyl)]-1,10-phenanthroline (0.098 g, 0.368 mmol), prepared as described by Example 2, were reacted to yield 0.066 g (65% yield) of the title methyl ether as a colorless oil: $^1$H NMR (300 MHz, CDCl$_3$) δ9.24 (dd, J=4.50, 1.80 Hz, H$_{p9}$), 8.23 (dd, J=8.40, 1.80 Hz, H$_{p7}$), 8.20 (d, J=8.40 Hz, H$_{p4}$), 7.97 (d, J=8.40 Hz, H$_{p3}$), 7.78 and 7.72 (two d, J=8.80 Hz, H$_{p5}$ and H$_{p6}$), 7.60 (dd, J=7.80, 4.50 Hz, H$_{p8}$), 3.24 (s, OCH$_3$), 2.34 and 2.24 (two dq, J=7.5 Hz, (CH$_2$CH$_3$)$_2$), 0.73 (t, J=7.50 Hz, (CH$_2$CH$_3$)$_2$); $^{13}$C NMR (75 MHz) δ164.85, 150.31, 146.45. 145.28, 136.10, 135.54, 128.89. 127.24, 126.55, 125.88, 122.48, 121.52, 84.26, 49.80, 28.17, 7.54; IR (CHCl$_3$) 2969 (C—H Ar), 2935 (CH), 910 (C—H Ar) cm$^{-1}$; HRMS m/e Calcd for C$_{18}$H$_{21}$N$_2$O (MH$^+$): 281.164, found, 281.1646.

Example 10

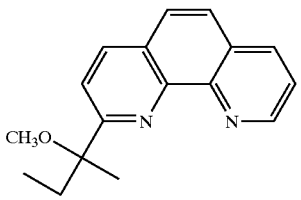

2-[(1-Methoxy-1-methylpropyl)]-1,10-phenanthroline

By following General Procedure II, NaH (0.034 g, 1.5 mmol), methyl iodide (0.091 mL, 1.5 mmol), and the corresponding 1-hydroxy-1-methylpropyl phenanthroline (0.092 g, 0.365 mmol) were reacted to provide 0.070 g (72% yield) of the title methyl ether as a colorless oil: $^1$H NMR (300 MHz, CDCl$_3$) δ9.24 (dd, J=4.65, 1.80 Hz, H$_{p9}$), 8.24 (one d, J=8.40 Hz, H$_{p4}$, one dd, J=8.10, 1.80 Hz, H$_{p7}$), 7.96 (d, J=8.40 Hz, H$_{p3}$), 7.82 and 7.75 (two d, J=8.70 Hz, H$_{p5}$ and H$_{p6}$), 7.62 (dd, J=8.10, 4.20 Hz, H$_{p8}$), 3.22 (s, OCH$_3$), 2.19 (q, J=7.50 Hz, CH$_2$CH$_3$), 1.83 (s, CH$_3$), 0.90 (t, J=7.50 Hz, CH$_2$CH$_3$); $^{13}$C NMR (75 MHz) δ165.87, 150.48, 146.48, 145.31, 136.11, 136.07, 128.90, 127.43, 126.48, 126.07, 122.52, 120.66, 82.06, 50.85, 32,66, 22.62, 7.96: IR (CHCl$_3$) 2970 (C—H Ar), 2932 (CH), 910 (C—H Ar), cm$^{-1}$; HRMS m/e Calcd for C$_{17}$H$_{19}$N$_2$O (MH$^+$): 267.1497, found, 267.1504.

Example 11

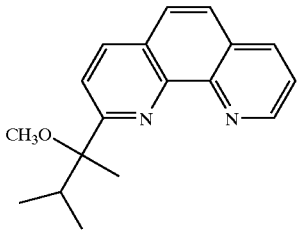

2-[(1-Methoxy-1,2-dimethylpropyl)]-1,10-phenanthroline

By employing General Procedure II, NaH (0.020 g, 0.74 mmol), methyl iodide (0.046 mL, 0.74 mmol), and the corresponding 1-hydroxy-1,2-dimethylpropyl phenanthroline (0.052 g, 0.185 mmol), prepared as described by Example 4, were reacted to yield 0.052 g (70% yield) of the title methyl ether as a colorless oil: $^1$H NMR (300 MHz, CDCl$_3$) δ9.24 (dd, J=4.40, 1.80 Hz, H$_{p9}$), 8.24 (dd, J=8.10, 1.80 Hz, H$_{p7}$), 8.11 (d, J=8.40 Hz, H$_{p4}$), 7.88 (d, J=8.40 Hz, H$_{p3}$), 7.81 and 7.74 (two d, J=8.80 Hz, H$_{p5}$ and H$_{p6}$), 7.60 (dd, J=8.10, 4.50 Hz, H$_{p8}$), 3.17 (s, OCH$_3$), 2.25 (sep, J=6.80 Hz, CH(CH$_3$)CH$_3$),1.88 (s, CH$_3$), 1.00 (d, J=6.60 Hz, CH(CH$_3$)CH$_3$), 0.71 (d, J=6.90 Hz, CH(CH$_3$)CH$_3$); $^{13}$C NMR (75 MHz) δ165.28, 150.46, 146.51, 145.13, 136.07, 135.76, 128.87, 127/39, 126.46, 126.07, 122.49, 121.06, 84.40, 51.25 39.10, 17.72, 17.43, 16.64; IR (CHCl$_3$ 2961 (C—H Ar), 2928 (CH), 866.4 (C—H Ar) cm$^{-1}$; HRMS m/e Calcd for C$_{18}$H$_{21}$N$_2$O (MH$^+$): 281.1654, found 281.1651.

Example 12

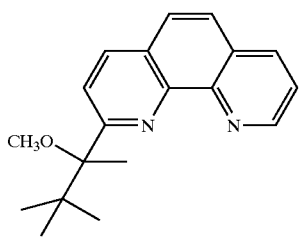

2-[(1-Methoxy-1,2,2-trimethylpropyl)]-1,10-phenanthroline

By employing General Procedure II, NaH (0.008 g, 0.3 mmol), methyl iodide (0.020 mL, 0.3 mmol), and the corresponding 1-hydroxy-1,2,2-trimethylpropyl phenanthroline (0.023 g, 0.08 mmol), prepared as described by Example 5, were reacted to provide 0.013 g (55% yield) of the title methyl ether as a colorless oil: $^1$H NMR (300 MHz, CDCl$_3$) δ9.23 (dd, J=4.50, 1.80 Hz, H$_{p9}$), 8.23 (dd, J=7.80, 1.80 Hz, H$_{p7}$), 8.17 (d, J=8.70 Hz, H$_{p4}$), 7.88 (d, J=8.40 Hz, H$_{p3}$), 7.81 and 7.74 (two d, J=8.70 Hz, H$_{p5}$ and H$_{p6}$), 7.60 (dd, J=8.00, 4.40 Hz, H$_{p8}$), 3.21 (s, OCH$_3$), 1.94 (s, CH$_3$), 0.98 (s, (CH$_3$)$_3$); $^{13}$C NMR (75 MHz) δ163.79, 150.37, 145.12, 143.90, 135.97, 134.34, 128.82, 127.18, 126.47, 125.99, 122.53, 121.43, 86.16, 51.36, 38.83, 26.10, 17.78; IR (CHCl$_3$) 2957 (C—H Ar), 2928 (CH), 857 (C—H Ar) cm$^{-1}$; HRMS m/e Calcd for C$_{19}$H$_{23}$N$_2$O (MH$^+$): 295.1810, found, 295.1818.

Example 13

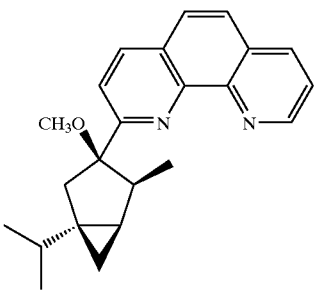

2-[(1S,3R,4S,5R)-(3-Methoxy-1-isopropyl-4-methylbicyclo[3.1.0]-hex-3-yl)-1,10-phenanthroline By following General Procedure II, NaH (0.120 g, 5.0 mmol), methyl iodide (0.70 mL, 5.0 mmol), and the corresponding hydroxybicyclo phenanthroline (0.430 g, 1.24 mmol), prepared as described by Example 6, there was obtained 0.334 g (75% yield) of the title methyl ether as a colorless oil: $^1$H NMR (300 MHz, benzene-d6) δ9.05 (dd, J=4.20, 1.8 Hz, H$_{p9}$), 7.68 and 7.65 (two d, J=8.40 Hz, H$_{p3}$ nd H$_{p4}$), 7.55 (dd, J=8.10, 4.20 Hz, H$_{p7}$), 7.33 and 7.23 (two d, J=8.80 Hz, H$_{p5}$ and H$_{p6}$), 6.92 (dd, J=8.10, 4.20 Hz, H$_{p8}$), 4.15 (dd, J=14.4, 1.80 Hz, C(OCH$_3$)CHH)), 2.95 (s, OCH$_3$), 2.75 (dq, J=6.90, 4.50 Hz, CHCH$_3$), 2.53 (d, J=14.4 Hz, C(OCH$_3$)CHH), 1.73 (sep, J=6.90 Hz, CH(CH$_3$)$_2$), 1.34 (t, J=3.90 Hz, cyclopropyl-H), 1.28 (two d, J=6.90 Hz, CH(CH$_3$)$_2$), 1.20 (ddd, J=4.20, 4.20, 3.90 Hz, cyclopropyl-H), 0.96 (d, J=6.90 Hz, CH(CH$_3$)$_2$), 0.40 (dd, J=7.8, 3.60 Hz, cyclopropyl-H); $^{13}$C NMR (75 MHz, benzene-d6) δ164.31, 150.24, 147.17, 146.49, 135.87, 135.32, 128.86, 127.48, 126.38, 126.08, 122.61, 120.33, 90.45, 50.77, 48.61, 33.88, 32.90, 30.17, 28.46, 20.82, 19.86, 11.43; IR (CHCl$_3$) 2958 (C—H Ar), 2868 (CH), 856 (C—H Ar), cm$^{-1}$; HRMS m/e Calcd for C$_{23}$H$_{27}$N$_2$O (MH$^+$): 347.2123; found, 347.2137.

Based on the NOE spectrum of the product ether the stereochemistry at C3 was concluded to be R. The spectrum gives crosspeaks for protons which are close in space and some of the crucial crosspeaks are shown in the partial formula below.

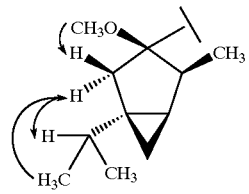

Example 14

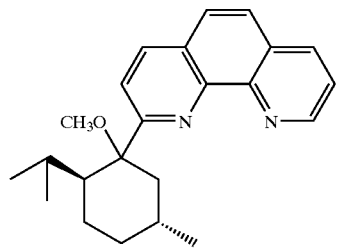

2-[(2R*,5S*,)-(1-Methoxy-2-isopropyl-5-methylcyclohexyl)]-1,10-phenanthroline

By using General Procedure II above, NaH (0.030 g, 1.2 mmol), methyl iodide (0.075 mL, 1.2 mmol), and the corresponding hydroxy phenanthroline, prepared as described by Example 7, (0.100 g, 0.298 mmol) were reacted to provide 0.092 g (88% yield) of the methyl ether title compound as a colorless oil; $^1$H NMR (300 MHz, CDCl$_3$) δ9.23 (dd, J=4.40, 1.80 Hz, H$_{p9}$), 8.24 (dd, J=8.05, 1.80 Hz, H$_{p7}$), 8.20 (d, J=8.40 Hz, H$_{p4}$), 7.90 (d, J=8.40 Hz, H$_{p3}$), 7.82 and 7.74 (two d, J=8.80 Hz, H$_{p5}$ and H$_{p6}$), 7.61 (dd, J=8.10, 4.20 Hz, H$_{p8}$), 3.22 (s, OCH$_3$), 2.64 (dd, J=14.7, 12.6 Hz, C(OCH$_3$)CHH), 2.23 (br dm, J=14.7 Hz, C(OCH$_3$)CHH), 1.80 (m, 4H), 1.60 (m, 1H), 1.46 (sep. J=6.90 Hz, CH(CH$_3$)$_2$), 1.29 (m, 1H), 1.05 (d, J=6.6 Hz, CHCH$_3$), 1.00 (d, J=6.90 Hz, CH(CH$_3$)CH$_3$), 0.56 (d, J=6.90 Hz, CH(CH$_3$)CH$_3$); $^{13}$C NMR (75 MHz) δ165.46, 150.42, 146.32, 136.19, 134.86, 128.85, 127.21, 126.58, 125.93, 122.50, 121.90, 85.86, 51.56, 50.39, 39.30, 34.74, 28.10, 26.82, 23.35, 22.44, 21.16, 18.23; IR (CHCl$_3$ 29.58 (C—H Ar), 28.68 (CH), 855.5 (C—H Ar) cm$^{-1}$; HRMS m/e Calcd for C$_{23}$H$_{29}$N$_2$O (MH$^+$): 349.2275, found, 349.2270.

General Procedure III

General Procedure for Samarium Diiodide Mediated Demethoxylation of 2-(Methoxyalkyl) phenanthrolines To a stirred solution of the 2-(1-methoxyalkyl) phenanthroline in THF was added a 0.1 M solution Of SmI$_2$ in THF (2.5 equiv.) at 25° C. The mixture was stirred at 25° C. and monitored by TLC. Upon completion of the reaction, a saturated aqueous solution of NH$_4$Cl was added to quench the reaction, and the resulting mixture was extracted with methylene chloride. The organic extracts were combined, washed with brine, dried over MgSO$_4$, filtered and concentrated. The product was purified by flash chromatography over alumina using an ethyl acetate/hexane gradient.

Example 15

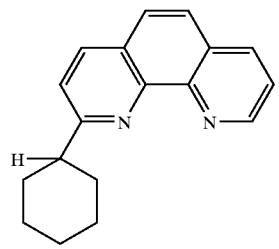

2-[(Cyclohexyl)]-1,10-phenanthroline

By following General Procedue III above, 0.1 M SmI$_2$ (17.1 mL, 1.71 mmol) was added to the 2-(1-methoxycyclohexyl)phenanthroline, prepared as described by Example 8, (0.200 g, 0.684 mmol) yielding 0.119 g (66% yield) of the title compound as a colorless oil: 1H NMR (300 MHz, CDCl$_3$) δ9.19 (dd, J=4.50, 1.80 Hz, H$_{p9}$), 8.16 (dd, J=8.10, 1.80 Hz, H$_{p7}$), 8.12 (d, J=8.40 Hz, H$_{p4}$), 7.71 and 7.64 (two d, J=8.80 Hz, H$_{p5}$ and H$_{p6}$), 7.54 (dd, J=8.10, 4.20 Hz, H$_{p8}$), 7.53 (d, J=8.40 Hz, H$_{p3}$), 3.33 (tt, J=3.00–3.30 Hz, ArCH), 2.12–1.28 (m, 10H, (CH$_2$)$_5$); $^{13}$C NMR (75 MHz) δ167.47, 150.21, 146.14, 145.34, 136.31, 135.86, 128.67, 127.05, 126.33, 125.35, 122.46, 120.48, 47.74, 33.28, 26.34, 26.04; IR (CHCl$_3$) 3049 (C—H Ar), 2929 (CH), 908 (C—H Ar) cm$^{-1}$; HRNS m/e Calcd for C$_{18}$H$_{19}$N$_2$O MH$^+$): 263.1548, found, 263.1534.

Example 16

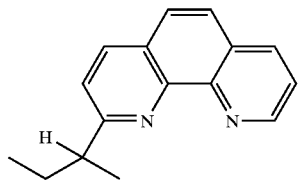

2-(1-methylpropyl)-1,10-phenanthroline

By using General Procedure III, 0.1 M SmI$_2$ (4.2 mL, 0.42 mmol) was added to the 2-(1-methoxy-1-methylpropyl)phenanthroline, prepared as described by Example 10, (0.045 g, 0.68 mmol) yielding 0.011 g (66% yield) or the title compound as a colorless oil: $^1$H NMR (300 MHz, CDCl$_3$) δ9.25 (dd, J=4.20, 1.50 Hz, H$_{p9}$) 8.24 (dd, J=7.80, 1.50 Hz, H$_{p7}$), 8.19 (d, J=8.40 Hz, H$_{p4}$), 7.79 and 7.71 (two d, J=8.70 Hz, H$_{p5}$ and H$_{p6}$), 7.61 (dd, J=8.10, 4.20 Hz, H$_{p8}$), 7.56 (d, J=8.40 Hz, H$_{p3}$), 3.43 (sext, J=7.20 Hz, CHCH$_3$), 1.90 and 1.77 (teo ddq, J=7.50 Hz, CH$_2$CH$_3$), 1.42 (d, J=7.20 Hz, CHCH$_3$), 0.96 (t, J=7.50 Hz, CH$_2$CH$_3$); $^{13}$C NMR (75 MHz) δ168.01, 150.21, 145.45, 144.83, 136.39, 136.09, 128.79, 127.14, 126.48, 125.43, 122.54, 120.46, 44.60, 30.23, 20.63, 12.13; IR (CHCl$_3$) 2966 (C—H Ar), 2931 (CH), 851 (C—H Ar) cm$^{-1}$; HRNS m/e Calcd for C$_{16}$H$_{17}$N$_2$O (MH$^+$): 237.1392, found, 237.1402.

Example 17

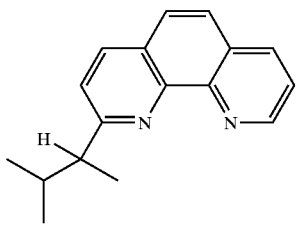

2-(1,2-Dimethylpropyl)-1-10-phenanthroline

By following General Procedure III, 0.1 M SmI$_2$ (4.6 mL, 0.46 mmol) was added to the corresponding 2-(1-methoxy-1,2-dimethylpropyl)phenanthroline, prepared as described by Example 11, (0.052 g, 0.18 mmol) yielding 0.27 g of the title compound as a colorless oil: $^1$H NMR (300 MHz, CDCl$_3$) δ9.24 (dd, J=4.40, 1.80 Hz, H$_{p9}$), 8.23 (dd, J=8.10, 1.80 Hz, H$_{p7}$), 8.18 (d, J=8.40 Hz, H$_{p4}$),7.79 and 7.72 (two d, J=8.80 Hz, H$_{p5}$ and H$_{p6}$), 7.60 (dd, J=8.10, 4.50 Hz, H$_{p8}$), 7.53 (d, J=8.40 Hz, H$_{p3}$), 3.24 (dq, J=6.90, 1.50 Hz, C HCH$_3$), 2.11 (dsep, J=6.90, 2.10 Hz, CH(CH$_2$), 1.41 (d, J=7.20 Hz, CHCH$_3$), 1.06 (d, J=6.30 Hz, CH(CH$_3$)CH$_3$); $^{13}$C NMR (75 MHz) δ162.06, 150.12, 147.35, 136.16, 135.76, 128.87, 127.39, 126.67, 125.37, 122.61, 121.32, 49.78, 33.81, 21.69, 19.96, 18.30; IR (CHCl$_3$) 2958 (C—H Ar), 2924 (CH), 852 (C—H Ar) cm$^{-1}$; HRMS m/e Calcd for C$_{17}$H$_{19}$N$_2$ (MH$^+$): 251.1548, found, 251.1531.

Example 18

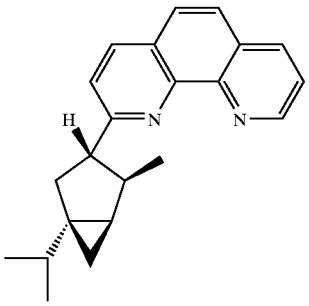

2-((1S,3S,4S,5R)-(1-isoPropyl-4-methylbicyclo [3.1.0]hex-3-yl))-1,10-phenanthroline By following the General Procedure III, 0.1 M SmI$_2$ (9.31 mL, 0.931 mmol) was added to the corresponding methoxy compound, prepared as described by Example 13, (0.129 g, 0.372 mmol) yielding 0.080 g (68% yield) of the title compound as a colorless oil: $^1$H NMR (300 MHz, CDCl$_3$) δ9.24 (dd, J=4.20, 1.80 Hz, H$_{p9}$), 8.21 (dd, J=8.10, 1.80 Hz, H$_{p4}$), 7.77 and 7.70 (two d, J=8.80 Hz, H$_{p5}$ and H$_{p6}$), 7.61 (d, J=8.10 Hz, H$_{p3}$), 7.60 (dd, J=8.10, 4.20 Hz, H$_{p8}$), 3.05 (ddd, J=10.80, 7.50 Hz, ArCH), 2.64 (dq, J=6.60, 4.20 Hz, CHCH$_3$), 2.31 (dd, J=12.30, 7.20 Hz, Ar(CH)CHH), 1.98 (br t, J=12.00 Hz, Ar(CH)CHH), 1.54 (sep, J=6.90 Hz, CH(CH$_3$)$_2$), 1.01 (two d, J=6.60 Hz, two CH$_3$), 0.90 (d, J=6.90 Hz, CH$_3$), 0.69 (br t, J=4.50 Hz, cyclopropyl-H), 0.57 (d, J=7.20 Hz, cyclopropyl-H), 0.25 (m, cyclopropyl-H); $^{13}$C NMR (75 MHz) δ165.17, 150.29, 146.24, 145.34, 136.24, 138.88, 128.78, 127.11, 126.35, 125.51, 122.48, 121.06, 51.40, 42.30, 38.04, 32.73, 32.48, 28.60, 19.99, 19.83, 16.73, 9.33; IR (CHCl$_3$) 3049 (C—H Ar), 2927 (CH), 8.59

Example 19

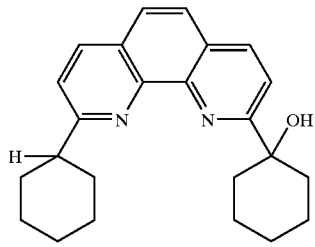

2-[(Cyclohexyl)]-9-[(1-hydroxycyclohexyl)]-1,10-phenanthroline

By following General Procedure I, cyclohexanone (0.094 g, 0.953 mmol) was added to 2-(cyclohexyl)-1,10-phenanthroline, prepared as described by Example 15, (0.100 g, 0.381 mmol) and 0.1 M $SmI_2$ (8.38 mL, 0.838 mmol) yielding 0.083 g (60% yield) of the title compound as a colorless oil: $^1$H NMR (300 MHz, $CDCl_3$) δ8.24 and 8.14 (two d, J=8.40 Hz, $H_{p3}$ and $H_{p9}$), 7.76 and 7.70 (two d, J=8.80 Hz, $H_{p5}$ and $H_{p6}$), 7.66 and 7.52 (two d, J=8.40 Hz, $H_{p4}$ and $H_{p7}$), 3.06 (tt, J=11.85, 3.30 Hz, $(CH_2)_5C\underline{H}$ (phenan)), 2.18–1.74 (m, 10H), 1.52–1.33 (m, 10H); $^{13}$C NMR (75 MHz) δ166.98, 165.25, 144.88, 143.44, 137.16, 136.01, 127.49, 127.28, 126.21, 124.85, 121.47, 118.65, 73.16, 47.24, 36.75, 32.81, 26.64, 26.12, 25.75, 22.71; IR ($CHCl_3$) 3338 (OH), 3042 (C—H Ar), 2927 (CH), 852 (C—H Ar) cm$^{-1}$; HRMS m/e Calcd for $C_{24}H_{29}N_2O$ (MH$^+$): 361.2280, found, 361.2272.

Example 20

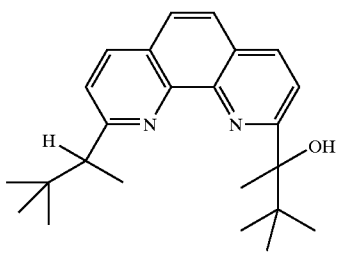

2-[(1,2,2-trimethylpropyl)]-9-(1-hydroxy-1,2,2-trimethylpropyl)]-1,10-phenanthroline By following General Procedure I, 2-[(1,2,2-trimethylpropyl)]-1,10-phenanthroline, is reacted with samarium diiodide and 3,3-dimethyl-2-butanone to provide the title compound.

Example 21

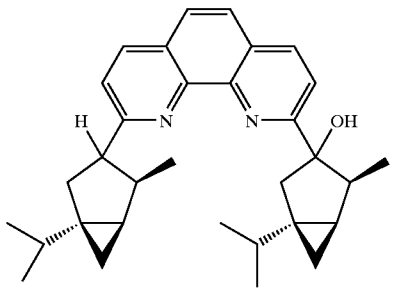

2-((1S,3S,4S,5R)-(1-isoPropyl-4-methylbicyclo[3.1.0]hex-3-yl))-9-((1S,3R,4S,5R)-(3-Hydroxy-1-isopropyl-4-methylbicyclo[3.1.0]hex-3-yl))-1,10-phenanthroline By following General Procedure I, 2-((1S,3S,4S,5R)-(1-isopropyl-4-methylbicyclo[3.1.0]hex-3-yl))-1,10-phenanthroline prepared as described by Example 18, is reacted with samarium diiodide and (−)-thujone to form the title compound.

Example 22

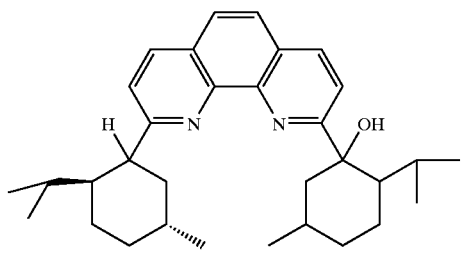

2-[(2R*,5S*,)-(2-isoPropyl-5-methylcyclohexyl)]-9-[(1-hydroxy-2-isopropyl-5-methylcyclohexyl)]-1,10-phenanthroline By following General Procedure I, the title compound is prepared in a mixture of diastereoisomers by reacting with samarium diiodide 2-[(2R*,5S*)-(2-isopropyl-5-methylcyclohexyl)]-1,10-phenanthroline and dl-menthone.

Example 23

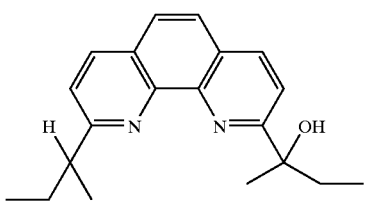

2-[(1-methylpropyl)]-9-[(1-hydroxy-1-methylpropyl)]-1,10-phenanthroline

The title compound is prepared by following the General Procedure I with samarium diiodide and 2-(2-butyl)-1,10-phenanthroline, prepared as described by Example 16, and 2-butanone.

Example 24

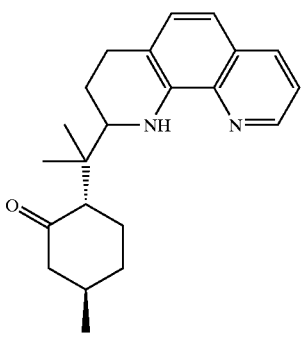

2-(1-Methyl-1-[(4R)-4-methyl-2-oxocyclohexyl]ethyl)-1,2,3,4-tetrahydrophenanthroline By following the General Procedure I, (R)-(+)-pulegone (0.186 g, 1.22 mmol) gave 0.092 g (50% yield) of the title compound as a colorless oil: $^1$H NMR (300 MHz, CDCl$_3$) δ8.66 (dd, J=3.90, 1.50 Hz, H$_{p9}$), 7.97 (dd, J=8.40, 1.80 Hz, H$_{p7}$), 7.28 (dd, J=8.40, 4.50 Hz, H$_{p8}$), 7.02 and 6.92 (two d, J=8.10 Hz, H$_{p5}$ and H$_{p6}$), 5.93 (br s, NH), 4.57 (br s, 1H), 2.71 (dt, J=11.6, 4.3 Hz, 1H), 2.46 (m, 2H), 2.25 (m, 1H), 2.10 (m, 2H), 1.93 (m, 3H), 1.24 (m, 3H), 1.1 (s, 3H), 1.09 (s, 3H), 0.92 (d, J=6.9 Hz, 3H); $^{13}$C NMR (75 MHz0 δ213.43, 147.20, 138.41, 136.58, 135.91, 128.85, 127.95, 122,86, 120.61, 112.90, 65.10, 60.32, 59.10, 59.01, 55.15, 29.44, 29.31, 29.04, 28.56, 27.47, 23.88, 19.80; IR (CHCl$_3$) 3436 (NH), 2956 (CH), 1688 (C=O), 909 (C—H Ar) cm$^{-1}$; HRMS m/e Calcd for C$_{22}$H$_{29}$N$_2$O (MH+): 335.2123, found, 335.2134.

Example 25

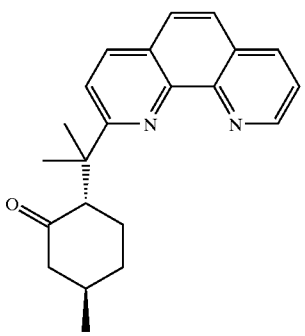

2-((1-methyl-1-[(4R)-4-methyl-2-oxocyclohexyl]ethyl)-1,10-phenanthroline

The title compound is prepared by reacting in THF the tetrahydrophenanthroline, obtained as described by Example 24, with DDQ.

I claim:

1. The process for preparing a compound of the formula

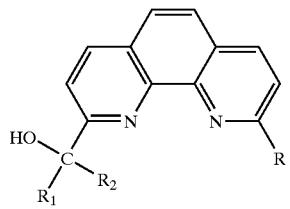

wherein

R is hydrogen, C$_1$–C$_{12}$ alkyl, cycloalkyl, cycloalkenyl, C$_1$–C$_4$-alkyl substituted by one or two cycloalkyl or cycloalkenyl groups wherein said cycloalkyl and cycloalkenyl have from 4 to 10 ring carbon atoms, or R is a bicycloalkyl or bicycloalkenyl group having from 6 to 8 carbon atoms in the bicylic ring;

R$_1$ and R$_2$ taken separately are independently C$_1$–C$_{12}$ alkyl, cycloalkyl, cycloalkenyl, C$_1$–C$_4$-alkyl substituted by one two cycloalkyl or cycloalkenyl groups, wherein said cycloalkyl and cycloalkenyl groups have from 4 to 10 ring carbon atoms; and wherein said R, R$_1$ and R$_2$ groups are optionally substituted by hydroxy, sulfhydryl, carboxy, amino or phosphono; which comprises mixing in an inert moderately polar solvent at a temperature between about 0° C. and about 75° C. a 1,10-phenanthroline of the formula

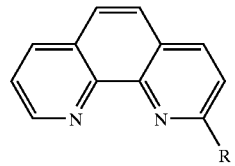

with a ketone R$_1$C(O)R$_2$ and a lanthanide II metal coupling reagent.

2. The process of claim 1 wherein R is hydrogen.

3. The process of claim 2 wherein R$_1$ and R$_2$ are C$_1$–C$_{12}$ and said alkyl optionally substituted by hydroxy, sulfhydryl, carboxy, amino or phosphono.

4. The process of claim 3 wherein R$_1$ is methyl, ethyl, isopropyl or t-butyl and R$_2$ is methyl or ethyl.

5. The process of claim 1 wherein R is other than hydrogen.

6. The process of claim 5 wherein R$_1$ is methyl, R$_2$ ethyl or t-butyl and R is 2-butyl or 1,2,2-trimethylpropyl.

7. The process of claim 5 wherein R$_1$ and R$_2$ are taken together to form a cycloalkyl, cycloalkenyl, bicycloalkyl or bicycloalkenyl group.

8. The process of claim 7 wherein R$_1$ and R$_2$ form 2-isopropyl-5-methylcyclohexyl and R is (2R*,5S*)-2-isopropyl-5-methylcyclohexyl.

9. The compound of the formula

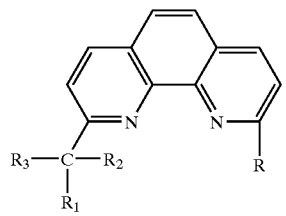

wherein

R is hydrogen, C$_1$–C$_{12}$ alkyl, cycloalkyl, cycloalkenyl, C$_1$ to C$_4$-alkyl substituted by one or two cycloalkyl or cycloalkenyl groups, wherein said cycloalkyl and cycloalkenyl groups have from 4 to 10 ring carbon atoms, or R is a bicycloalkyl or bicycloalkenyl group each having from 6 to 8 carbon atoms in the bicyclic ring;

R$_1$ and R$_2$ taken separately are independently C$_1$–C$_{12}$ alkyl, cycloalkyl or cycloalkenyl, C$_1$ to C$_4$-alkyl substituted by one or two cycloalkyl or cycloalkenyl groups, wherein said cycloalkyl and cycloalkenyl groups have from 4 to 10 ring carbon atoms; and wherein said R, R$_1$ and R$_2$ groups are optionally substituted by hydroxy, sulfhydryl, carboxy, amino or phosphono; and R$_3$ is hydroxy.

10. The compound of claim 9 wherein R is hydrogen.

11. The compound of claim 10 wherein $R_1$ is methyl, ethyl, isopropyl or t-butyl and $R_2$ is methyl or ethyl.

12. The compound of claim 9 wherein $R_3$ is hydroxy or sulfhydryl and R is other than hydrogen.

13. The compound of claim 12 wherein $R_1$ is methyl, $R_2$ is methyl, ethyl or t-butyl and R is 2-butyl or 1,2,2-trimethylpropyl.

14. The compound of claim 10 wherein $R_1$ and $R_2$ are taken together with the carbon to which they are bonded to form a cycloalkyl, cycloalkenyl, bicycloalkyl or bicycloalkenyl group.

15. The compound of claim 14 wherein $R_1$ and $R_2$ form cyclohexyl, [(1S,3R,4S,5R)-1-isopropyl-4-methylbicyclo[3.1.0]hex-3-yl] or 2-isopropyl-5-methylcyclohexyl.

16. The compound of claim 12 wherein $R_3$ is hydroxy, $R_1$ and $R_2$ form [(1S,3R,4S,5R)-1-isopropyl-4-methylbicyclo[3.1.0]hex-3-yl] and R is [(1S,3R,4S,5R)-1-isopropyl-4-methylbicyclo[3.1.0]hex-3-yl] said compound being 2-[(1S,3S,4S,5R)-(3-hydroxy-1-isopropyl-4-methylbicyclo[3.1.0]hex-30-yl]-9-[(1S,3S,4S,5R)-(1-isopropyl-4-methylbicyclo[3.1.0]hex-3-yl)]-1,10-phenanthroline.

17. The compound of claim 12 wherein $R_3$ is hydroxy, said compound being 2-[(2-isopropyl-5-methylcyclohexyl)]-9-[(1-hydroxyl-2-isopropyl-5-methylcyclohexyl)]-1,10-phenanthroline.

18. The compound of claim 9 wherein $R_3$ is and acyl group of the formula a) or an ether group of the formula b) wherein y is O.

19. The compound of claim 18 wherein $R_3$ is an ether group b), $R_4$ is methyl and $R_1$ and $R_2$ are taken together with the carbon to which they are bonded to form a cycloalkyl, cycloalkenyl, bicycloalkyl or bicycloalkenyl group.

20. The compound of claim 19 wherein $R_1$ and $R_2$ form (1S,3R,4S,5R)-(1-isopropyl-4-methylbicyclo03.1.0]hex-3-yl and R is hydrogen.

21. The process of claim 2 wherein $R_1$ and $R_2$ are taken together to form a cycloalkyl, cycloalkenyl, bicycloalkyl or bicycloalkenyl group.

22. The process of claim 21 wherein $R_1$ and $R_2$ form (1S,3R,4S,5R)-(1-isopropyl-4-methylbicyclo(3.1.0)hex-3-yl.

23. The process of claim 1 wherein the lanthanide II metal coupling reagent is samarium II.

24. The compound of claim 11 said compound being 2-[(1-hydroxy-1-ethylpropyl)]-1-10-phenanthroline.

25. The compound of claim 11 said compound being 2-[(1-hydroxy-1-methylpropyl)]-1-10-phenanthroline.

26. The compound of claim 11 said compound being 2-[(1-hydroxy-1,2-dimethylpropyl)]-1-10-phenanthroline.

27. The compound of claim 11 said compound being 2-[(1-hydroxy-1,2,2-trimethylpropyl)]-1-10-phenanthroline.

28. The process if claim 1 wherein methyl ethyl ketone is coupled with 1,10-phenanthroline to provide 2-[(1-hydroxy-1-methylpropyl)]-1,10-phenanthroline.

29. The process of claim 1 wherein methyl isopropyl ketone is coupled with 1,10-phenanthroline to provide 2-[(1-hydroxy-1,2-dimethylpropyl)]-1,10-phenanthroline.

30. The process of claim 1 wherein methyl t-butyl ketone is coupled with 1,10-phenanthroline to provide 2-[(1-hydroxy-1,2,2-trimethylpropyl)]-1,10-phenanthroline.

* * * * *